United States Patent [19]

Frost et al.

[11] Patent Number: 5,599,421
[45] Date of Patent: Feb. 4, 1997

[54] DISPOSAL UNIT

[75] Inventors: Frederick C. Frost; Edward T. Williams; Peter Saunders, all of Essex, United Kingdom

[73] Assignee: F C Frost Limited, Essex, United Kingdom

[21] Appl. No.: 232,220

[22] PCT Filed: Nov. 4, 1992

[86] PCT No.: PCT/GB92/02033

§ 371 Date: Aug. 10, 1994

§ 102(e) Date: Aug. 10, 1994

[87] PCT Pub. No.: WO93/09043

PCT Pub. Date: May 13, 1993

[30] Foreign Application Priority Data

Nov. 5, 1991 [GB] United Kingdom ............... 9123445

[51] Int. Cl.$^6$ ........................................... B32B 31/00
[52] U.S. Cl. .................... 156/359; 156/366; 156/515; 156/358; 53/555; 221/12; 221/15; 221/152
[58] Field of Search ............... 156/366, 358, 156/359, 515; 219/385, 489, 490, 491, 492, 493, 496; 53/373.7, 374.3, 553, 555; 221/12, 13, 15, 151, 152, 153

[56] References Cited

U.S. PATENT DOCUMENTS

| 4,025,383 | 5/1977 | Ferrigno ............................ 156/530 |
|---|---|---|
| 4,341,583 | 7/1982 | Schwarz ............................ 156/359 |
| 4,378,266 | 3/1983 | Gerken ............................. 156/359 |
| 4,650,535 | 3/1987 | Bennett et al. .................. 156/358 X |
| 4,761,197 | 8/1988 | Christine et al. ................ 156/358 X |
| 4,804,107 | 2/1989 | Bergstedth ........................ 221/12 |
| 4,981,236 | 1/1991 | Riedle et al. .................. 221/151 X |
| 5,143,251 | 9/1992 | Kahanek et al. .................. 221/152 |
| 5,221,024 | 6/1993 | Campbell ..................... 221/15 X |

FOREIGN PATENT DOCUMENTS

| 2413065 | 3/1976 | Germany . |
| 1063119 | 3/1967 | United Kingdom . |
| 2203326 | 10/1988 | United Kingdom . |

*Primary Examiner*—James Engel
*Assistant Examiner*—Paul M. Rivard
*Attorney, Agent, or Firm*—Nixon & Vanderhye P.C.

[57] ABSTRACT

A disposal unit for sanitary towels comprises a housing (100) which supports a bag (1) for receiving the used towels. A door (4) is mounted to the housing, in use the door being opened for access to the bag. The unit includes a heat sealing device (8) operable when the door is in the closed position to seal hermetically the mouth of the bag. The door may be pivotally mounted at its lower edge to the housing in which case the means for supporting the bag are arranged to support the bag with the mouth of the bag located towards the top of the door. A control circuit may activate the heat sealing device for a predetermined period of time and also activate a solenoid which locks the door closed.

13 Claims, 6 Drawing Sheets

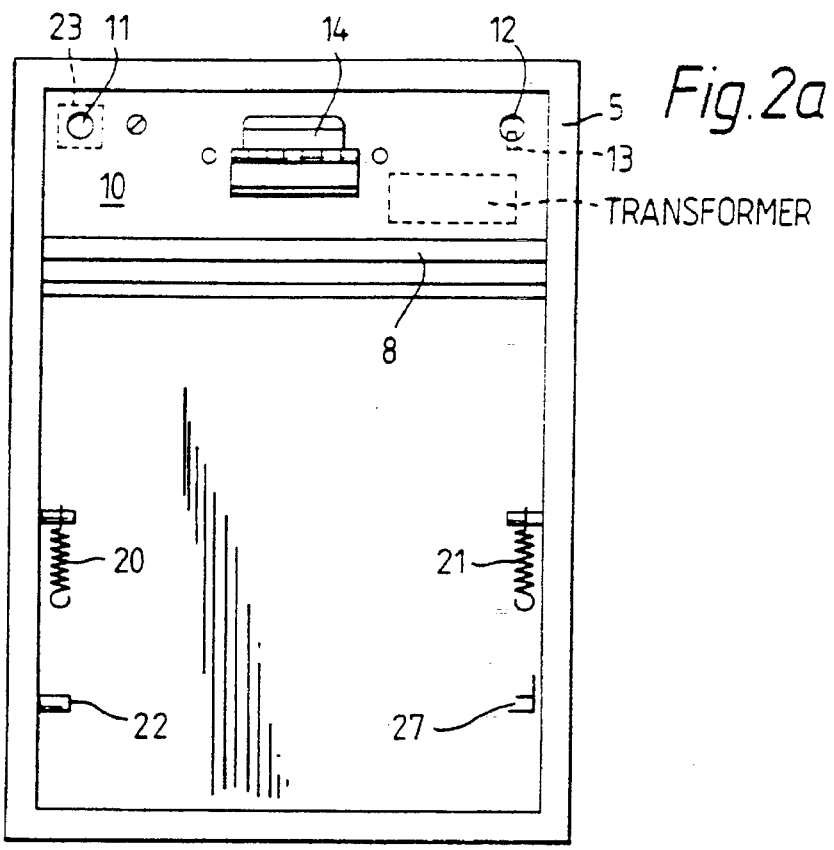
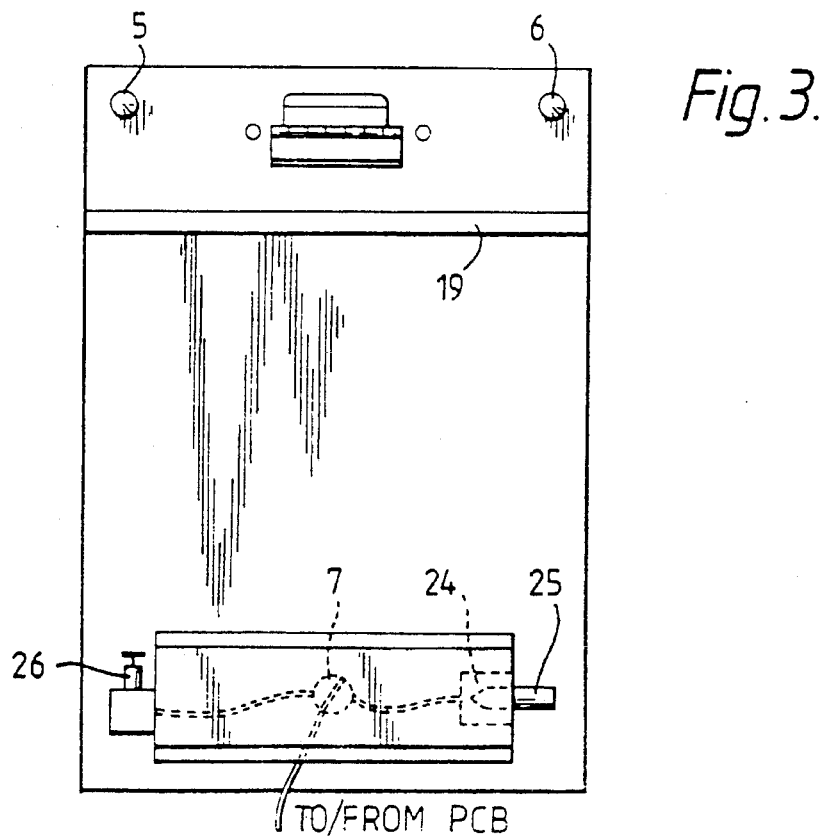

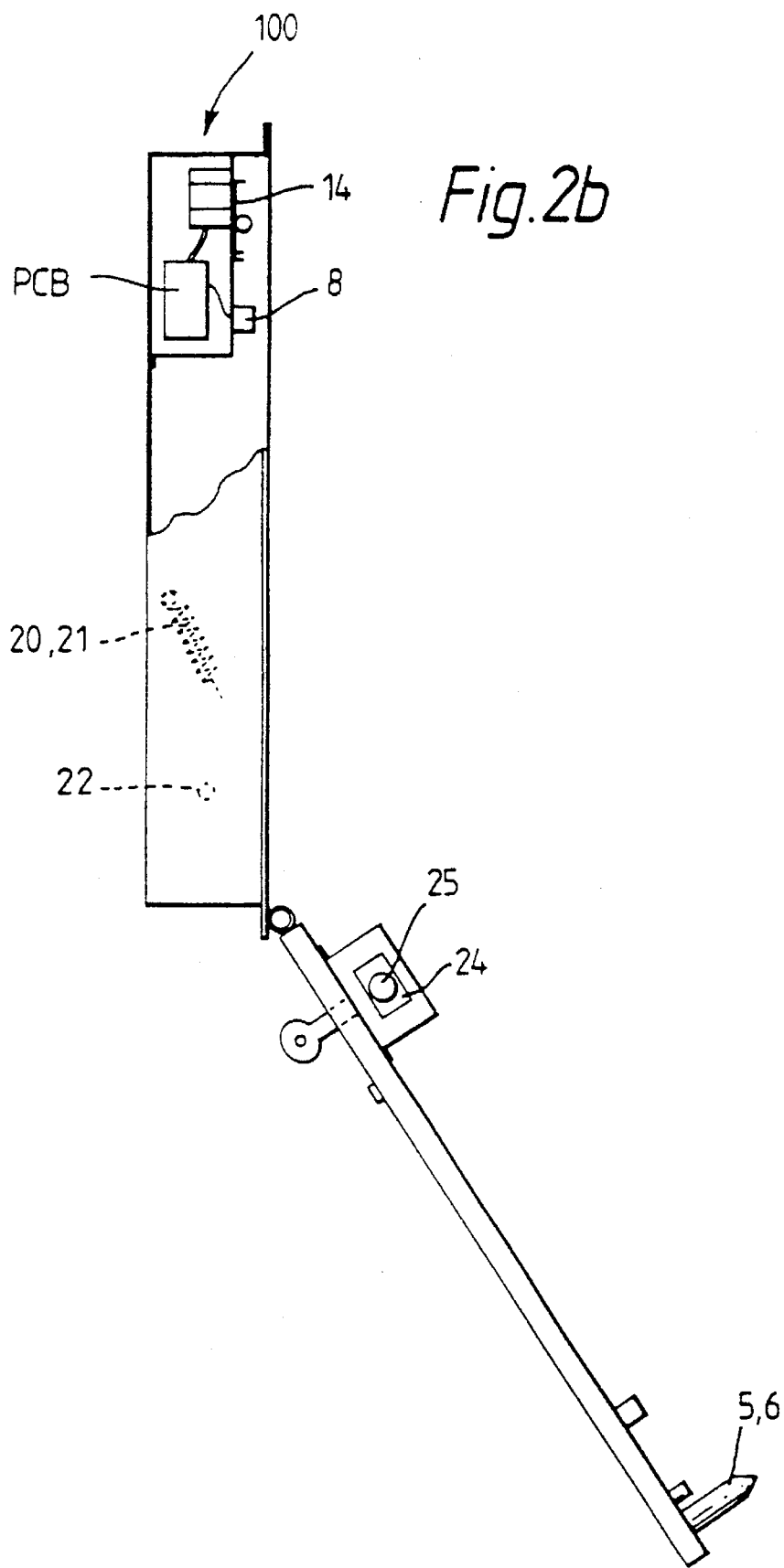

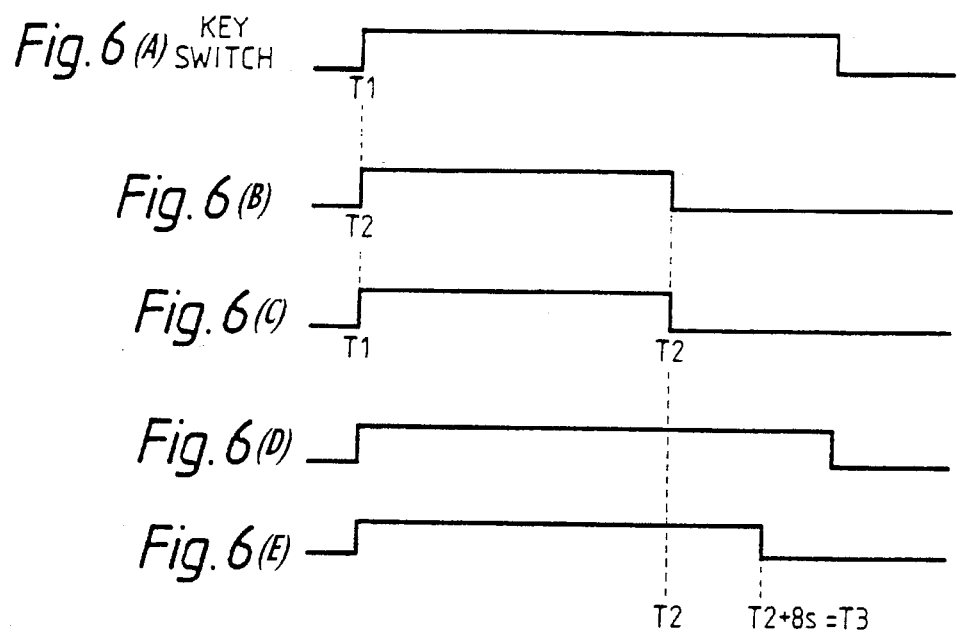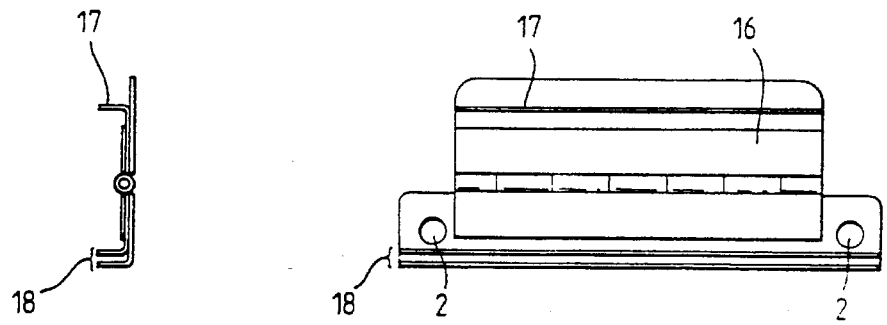

DISPOSAL UNIT

FIELD OF THE INVENTION

The present invention relates to a disposal unit for used sanitary towels.

SUMMARY OF THE INVENTION

According to the present invention, there is provided a disposal unit for sanitary towels comprising a housing, means for supporting a bag for receiving the used towels within the housing, a door mounted to the housing, in use the door being opened for access to the bag, and heat sealing means operable when the door is in the closed position to seal hermetically the mouth of the bag.

The present invention provides a unit in which the heat sealing of the bag can be carried out automatically within the closed unit, prior to the removal of the bag by the janitor. This greatly reduces the health risk involved, since the janitor does not have to open the unit until the bag has been sealed. The preferred aspects of the invention as set out below and defined in the claims offer the further advantage that electrical power is required only when the janitor comes to heat seal the unit and not during the normal use of the unit during the day.

Preferably the door is pivotally mounted at its lower edge to the housing and the means for supporting the bag are arranged to support the bag with the mouth of the bag located towards the top of the door.

DESCRIPTION OF THE DRAWINGS

FIG. 2a and 2b are a front elevation and partially cut-away side elevation of the main body of the unit;

FIG. 3 is a rear elevation of the door of the unit;

FIG. 6(a)–6(e) are a timing diagram; and

FIG. 7 shows the clamp.

DESCRIPTION OF AN EXAMPLE

Figure 1:
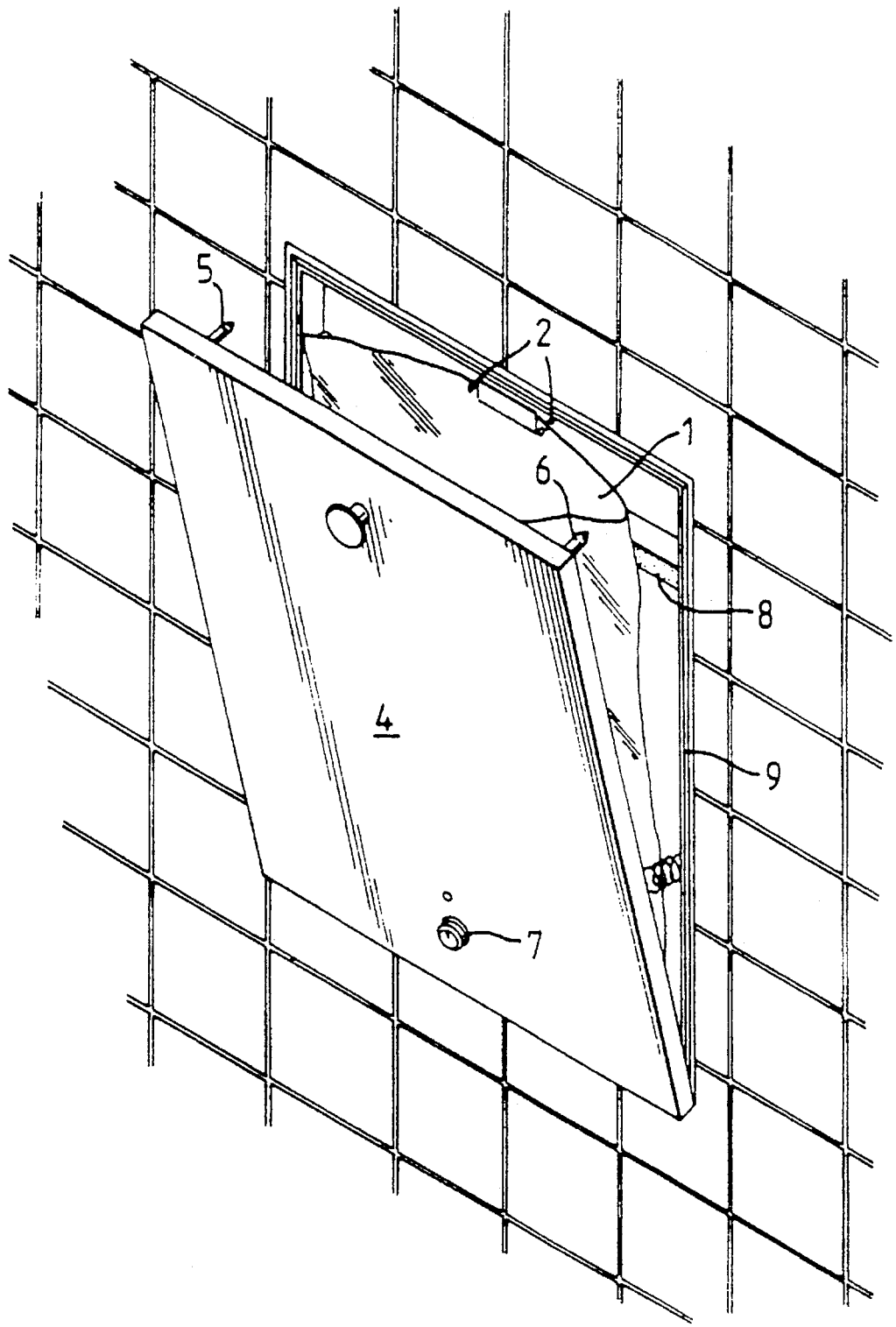
FIG. 1 is an isometric view of a unit mounted in a wall.

The unit takes used sanitary towels which are disposed of in a heat sealed plastic bag, thereby providing a hygienic method of disposal, the used product not being handled by anyone other than the user.

A plastic bag 1 is placed in the unit and is located by two stainless steel pins 2 for easy alignment and is clamped into position by a bracket or clamp 14 which is self-releasing on one side after the bag has been heat sealed. The unit is designed with a metal pin which is controlled by a solenoid. In normal use, the pin limits the movement of the door 4 to open to a position sufficient for the soiled material to be disposed of. After disposal by the user, the door is self-closing by means of two tension springs and therefore the plastic bag is closed, minimising odours. A position for a deodorant block is also provided within the housing.

Near to the top of the door, two metal machined dowels 5,6 are located, one either side of the door. One passes through an orifice 11 which when energised by the key switch pulls the door in tight and holds this position during the heat seal cycle. At the same time, the other dowel operates a microswitch after it has been energised by the key switch 7. The purpose of this microswitch and dowel is to prevent the low heat seal element 8 coming into operation when the door is open and the key switch has inadvertently been turned on. This is a safety feature.

A 12 volt transformer circuit board PCB and adjustable time controller is placed at the rear of the unit and is protected by a sub-housing 10. The time controller can be adjusted from the front. These components control the low voltage heat seal element 8 which is placed along the face of the metal casing and the full width of the unit. The heat seal element is encased in a teflon adhesive tape.

The door is cushioned by a seal 9 attached to the flange of the housing and around its perimeter. This gives the movement required when the heat seal element is brought into operation.

The sequence of operation for heat sealing the plastic bag is as follows:

1. The door is in a closed position.
2. An electrical two position key operated switch is located near the base of the door. The off position of the switch is at 12 o'clock.
3. The janitor rotates the key switch clockwise to the 3 o'clock position which energises a dowel and the microswitch as previously described. At the same time, a LED is initiated indicating that the heating element is in operation. This operation energises the heating element and seals the plastic bag. The LED light stays on for a further 8 seconds to make sure the seal has set.
4. When the LED light has gone off, this indicates that the bag has been sealed. The janitor then opens the door. This automatically releases the plastic bag from the clip on the back box side and also fully releases the metal pin to stop the door closing. The janitor can now remove the sealed bag by unclipping from the door side. He then fixes a new bag on the locating pins and clamps down firmly on the back box side pulling the door open which releases the automatic pin. After closing the door the automatic pin is released and will prevent the door opening to the fully open position in normal use. The door can now be opened to the user's normal position, the other side of the plastic bag is positioned onto the locating pins and clamped down firmly on the rear side of the door. The key is returned to the 12 o'clock position and removed. The unit is now ready for use.

FIG. 2a shows a plan of the main body of unit, that is the part which is normally recessed within the wall, the door removed for clarity. A sub-housing 10 at the top of the unit has orifices 11, 12 formed to receive the correspondingly positioned metal dowels on the inside face of the door. The first orifice 11, has associated with it a solenoid 23 which, when activated, holds fast the metal dowel. The other orifice 12, has a microswitch 13 positioned immediately under it and arranged to be operated by the insertion of the corresponding metal dowel into the orifice. This switch provides a safety interlock to prevent operation of the heating element with the door open. The control circuit is arranged only to supply power to the heating element if the microswitch has been operated by the insertion of the corresponding dowel.

The sub-housing 10 also supports a clamp 14 for the plastic bag and the heating element 8.

The clamp is shown in greater detail in FIG. 7. It includes a hinged flap 16 which holds down over the inner face of one side of the bag. A projecting lip 17 pushes the bag between two up-standing walls 18. The lip and the corresponding walls are configured so as to make a forced fit. A clamp of corresponding design is also positioned towards the top of the inside face of the door. It also makes a forced fit with the other side of the mouth of the bag. This clamp on the door is arranged to have a somewhat tighter fit than the clamp on the body of the unit, so that when the door is pulled open by the janitor after the heat sealing of the bag, the bag is held by the clamp on the door and falls free from the clamp mounted on the main body of the unit.

The heating element 8 is formed from tungsten and is mounted on an EPDM rubber block between a pair of upstanding walls which run across the width of the sub-housing. The tungsten element is covered with Teflon.

A corresponding positioned bar 19 mounted on the inside face of the door is brought into opposition with the bar supporting the heating element when the door is closed.

FIG. 2B shows the unit with the door fully opened beyond its normal position, in a configuration which might be used for example when the unit is being cleaned or serviced. As can be seen in this Figure, there are provided coiled springs 20,21 fixed about halfway along the length of the sides of the main body of the unit. In normal use, the other ends of these springs are attached to the door to bias the door towards the closed position. There is also formed on one of the side walls of the main body, towards the bottom of the unit, a stop 22 which in use co-operates with a further dowel 25 mounted towards the bottom of the door to limit the opening of the door. This further dowel is operated by a second solenoid 24. In normal use, this dowel projects outwards and by interference with the stop prevents the door from opening beyond the relatively small angle shown in FIG. 1. However, the dowel can be retracted by the solenoid to allow the door to be fully opened as further described below.

The sequence of operation for heat sealing the plastic bag outlined above will now be described in further detail with reference to the timing drawings in FIG. 6.

In normal use, SOLENOID 1 (i.e. the solenoid associated with the orifice in the sub-housing in the main body of the unit), SOLENOID 2 (i.e. the solenoid associated with the metal dowel mounted transversely towards the bottom of the door), and the heating element are all OFF. The door can then be opened by the user against the bias of the coil springs to a position limited by interference between the transverse dowel on the door and the stop on the side wall of the main body.

At time T1, the janitor operates the key switch at the bottom of the door. In response to this SOLENOID 1, SOLENOID 2, the heating element and the LED are all turned ON. SOLENOID 1 then holds the door firmly shut and in combination with the springs serves to apply pressure to the region of the mouth of the bag trapped between the heating element and the opposing bar on the inside face of the door. The heating element then heat seals the bag in this region. The transverse dowel is withdrawn into the solenoid, so as to be clear of the stop when the door is subsequently opened.

At a time T2 determined by the control circuit, the heating element and SOLENOID 1 are turned OFF. The duration of the heating period from T1 to T2 may be adjusted by the operator by means of the adjuster, which may be a variable potentiometer, mounted in the sub-housing and connected to the control circuit. This facilitates the use of the unit with different types of bags requiring different times to form an effective heat seal. In the present example the possible range of durations from T1 to T2 is 5 to 20 seconds.

At time T3, a fixed period, e.g. 8 seconds, after T2, the control circuit turns OFF the LED. The janitor then opens the door. At this time SOLENOID 2 is still ON and the transverse dowel withdrawn, so the door opens beyond the stop. As the door pivots beyond the stop a plunger switch 26 mounted on the other side of the inner face of the door to the transverse dowel strikes a bracket 27 mounted on the inside wall of the unit. This latches the switch OFF and so turns off the power to SOLENOID 2 which is connected in series with this switch. The transverse dowel is then spring biased into its extended position, so that interference between the dowel and the stop holds the door open against the force of the springs, facilitating access to the heat-sealed bag by the janitor.

After fitting a new bag into the unit the janitor pulls the door further open to operate the plunger switch again, causing that switch to toggle ON returning power to SOLENOID 2. This withdraws the dowel, allowing the door to be fully closed. The key is then turned back and withdrawn setting the unit back to its original state with the heating element and solenoids all OFF.

If for any reason manual control of the unit, independent of the control circuit is required, then this is possible by opening the unit and controlling SOLENOID 2 directly by means of the plunger switch.

Figure 4:
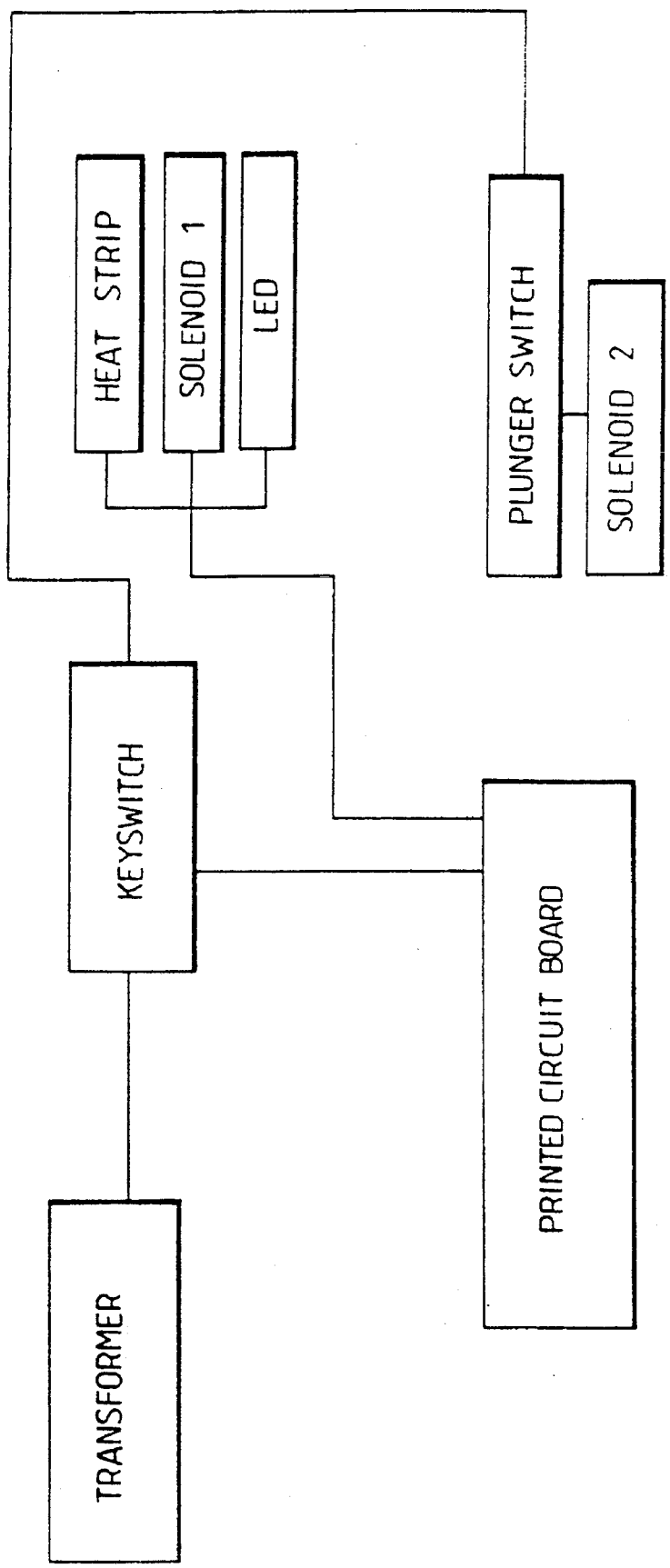
FIG. 4 is a block diagram.

The block diagram of FIG. 4 shows the relationship between the different elements of the unit. It will be apparent from the above description that the unit is designed so that it uses purely mechanical functions in normal operation, and only requires electrical power when the janitor seals and removes the bag. Accordingly the keyswitch is connected between the transformer and the PCB control circuit so that the latter is only powered up when the keyswitch is operated. The transformer in this example provides a 12V DC output from a 240V input.

Figure 5:
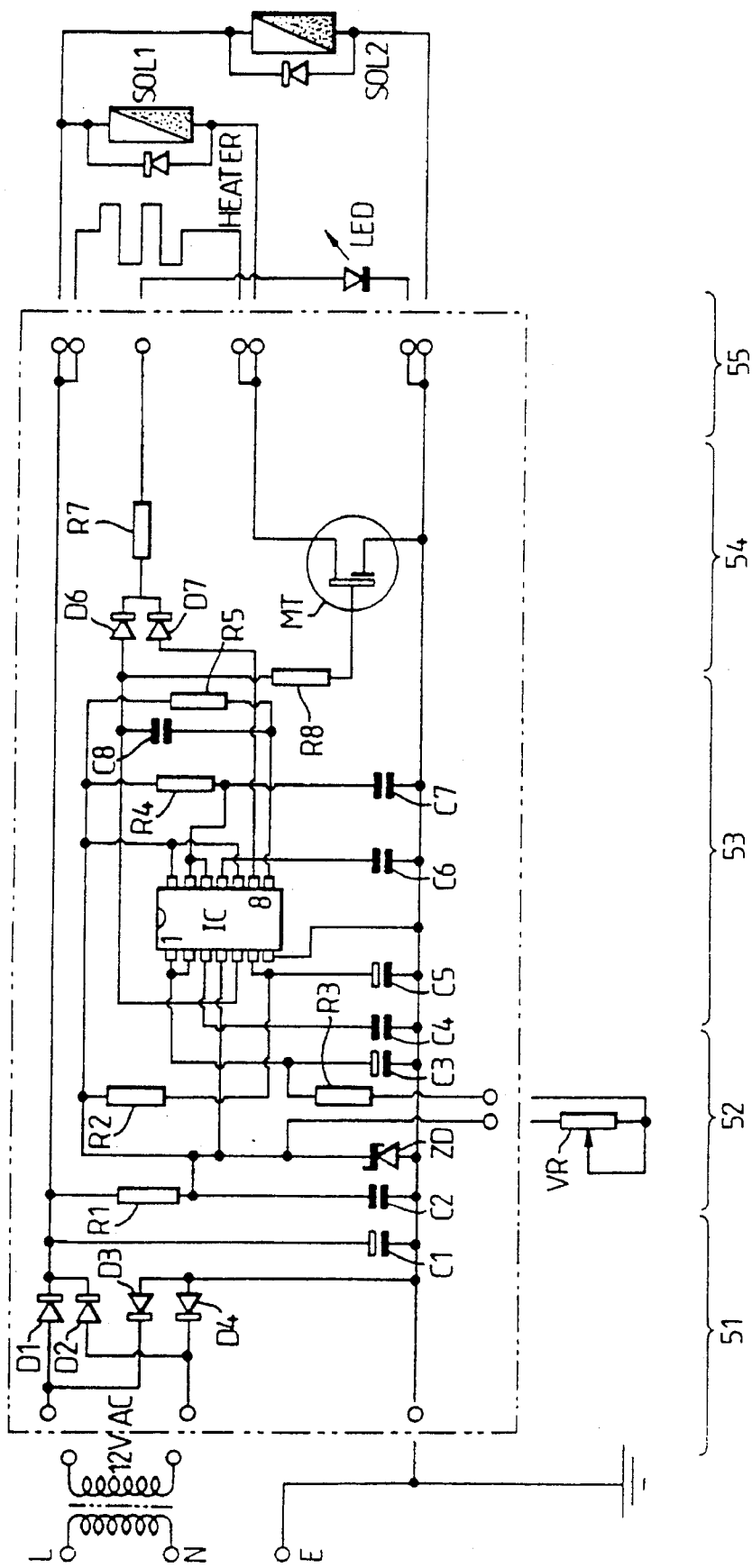
FIG. 5 is a circuit diagram of the control circuit.

FIG. 5 is a circuit diagram of the PCB control circuit. The component values are listed in Table 1. Table 2 is a key to the timing diagrams of FIGS. 6(*a*)–6(*e*). The control circuit comprises a power supply stage 51, a time adjust stage 52, timing components (including a timer IC) 53, a power switching stage 54 and a power output stage 55.

TABLE 1

| FROST HEAT SEALER CONTROL | |
|---|---|
| PARTS LIST | |
| D1 | Diode Type 1N5401 |
| D2 | " |
| D3 | " |
| D4 | " |
| D5 | Diode Type 1N4148/914/916 |
| D6 | " |
| D7 | " |
| D8 | Diode Type 1N4002/3/4 |
| D9 | " |
| D10 | Diode Type 1N4002/3/4 (not on PCB) |
| D11 | Diode Type 1N4002/3/4 (not on PCB) |
| ZD | Zener Diode 9V1/1W3 |
| IC | Dual Timer IC NE556 |
| DT | Darlington Transitype BDX53 |
| LED | Any Standard Type |
| C1 | Capacitor Electlytic 1000/16 V |
| C2 | Capacitor Electlytic 100/10 V |
| C3 | Capacitor Bead Tant 22/10 V |
| C4 | Capacitor Bead Tant 0.1/10 V |
| C5 | Capacitor Bead Tant 22/10 V |
| C6 | " |
| C7 | Capacitor Bead Tant 22/10 V |
| C8 | Capacitor Poly 0.001/(low) |
| R1 | Resistor OW5 47R |
| R2 | Resistor Ow25 33K |
| R3 | Resistor Ow25 330K |
| R4 | Resistor Ow25 330K |
| R5 | Resistor Ow25 33K |
| R6 | Resistor Ow25 4K7 |

TABLE 1-continued

FROST HEAT SEALER CONTROL

PARTS LIST

| R7 | Resistor 0w25 470R |
| --- | --- |
| R8 | Resistor 0w25 390R |
| VR | Linear Potentiometer 1 MO (not on PCB) |

TABLE 2

| 6a | Key Switch |
| --- | --- |
| 6b | Heat Strip |
| 6c | SOLENOID 1 |
| 6d | SOLENOID 2 |
| 6e | LED |

We claim:

1. A disposal unit for used sanitary towels comprising:

a housing;

means for supporting a bag for receiving the used towels within the housing;

a door mounted to the housing, in use the door being opened for access to the bag;

heat sealing means operable when the door is in the closed position to seal hermetically the mouth of the bag;

a solenoid-controlled interference member; and a stop, the interference member in combination with the stop comprising a means for limiting the opening of the door to a predetermined position, and, movable under solenoid control, to a position in which the interference member clears the step, for allowing opening of the door beyond the predetermined position.

2. A unit according to claim 1, in which the door is pivotally mounted at its lower edge to the housing and the means for supporting the bag are arranged to support the bag with the mouth of the bag located towards the top of the door.

3. A unit according to claim 1, in which the means for supporting the bag include releasable clamps mounted on the main body of the housing and on the inside face of the door respectively, in use, each clamp holding one side of the mouth of the bag, so that the mouth of the bag is opened as the door is opened.

4. A unit according to claim 1, in which the heat-sealing means include an elongate heating element extending across the inside of the housing, and means operable when the door is in the closed position to apply pressure to the bag along the region of contact with the elongate heating element.

5. A unit according to claim 4, in which the means to apply pressure include electromagnetic means operable to apply a closing force to the door, and an elongate bar which, when the door is closed, presses on the bag in opposition to the elongate heating element.

6. A unit according to claim 5, in which the electromagnetic means comprise a solenoid mounted on one of the door and the housing, and a metal dowel positioned to enter the orifice of the solenoid and fixed to the other of the door and the housing.

7. A unit according to claim 1, including control means which in response to the activation of a switch by the user simultaneously turn ON the means for heat sealing for a predetermined period of time and turn ON locking means for holding the door closed.

8. A unit according to claim 1, wherein said stop is mounted on one of the housing and the door, and the interference member is mounted on the other of the housing and the door, the interference member being resiliently biased into an extended position in which it interferes with the stop to limit the movement of the door, and being drawn back under solenoid control into a retracted position in which it clears the stop.

9. A unit according to claim 8, in which the control means are further arranged to turn ON the solenoid to retract the interference member in response to the activation of the switch, the control means being arranged to turn OFF the locking means after the heat sealing of the bag, and the door then being free for opening beyond the stop to facilitate removal of the bag.

10. A unit according to claim 1 in which the door is spring-biased into its closed position.

11. A unit according to claim 10, including a switch connected in series with the solenoid associated with the interference member, the switch being toggled OFF in response to the initial opening of the door beyond the position of the stop, thereby causing the interference member to extend and to hold the door open against the bias of the springs by interference with the stop.

12. A unit according to claim 7, in which the switch activated by the user is a key switch mounted on the outer face of the unit.

13. A disposal unit for used sanitary towels comprising:

a housing;

means for supporting a bag for receiving the used towels within the housing;

a door mounted to the housing, said door being openable for access to the bag;

heat sealing means operable when the door is in the closed position to seal hermetically the mouth of the bag;

a solenoid-controlled interference member;

a stop, the interference member in combination with the stop comprising a means for limiting the opening of the door to a predetermined position, and, movable under solenoid control to a position in which the interference member clears the stop, for allowing opening of the door beyond the predetermined position; and a key switch mounted on to the outer face of the unit for controlling operation of said solenoid-controlled interference member.

\* \* \* \* \*